United States Patent [19]

Hayashi et al.

[11] Patent Number: 4,857,543

[45] Date of Patent: Aug. 15, 1989

[54] THIOPHENE DERIVATIVE AND PROCESS FOR PREPARING THE SAME

[75] Inventors: Kimiaki Hayashi, Suita; Yasuhiko Ozaki, Neyagawa; Kenji Yamada, Saitama; Hideyuki Takenaga, Urawa; Ichizo Inoue, Kawanishi, all of Japan

[73] Assignee: Tanabe Seiyaku Co., Ltd., Osaka, Japan

[21] Appl. No.: 214,200

[22] Filed: Jun. 27, 1988

[30] Foreign Application Priority Data

Jun. 30, 1987 [JP] Japan .................. 62-164837

[51] Int. Cl.$^4$ ............... A61K 31/38; C07D 409/00; C07D 333/12
[52] U.S. Cl. .................. 314/444; 514/438; 549/60; 549/75; 549/77
[58] Field of Search ............ 549/74, 75, 60, 77; 514/438, 444

[56] References Cited

U.S. PATENT DOCUMENTS 3,122,561 2/1964 Cason et al.
4,128,551 12/1978 Braye .................. 549/74

FOREIGN PATENT DOCUMENTS 1343527 1/1974 United Kingdom .

OTHER PUBLICATIONS

Chemical Abstracts 99: 175393b.

Primary Examiner—Alan Siegel
Attorney, Agent, or Firm—Birch, Stewart, Kolasch & Birch

[57] ABSTRACT

A thiophen derivative of the formula:

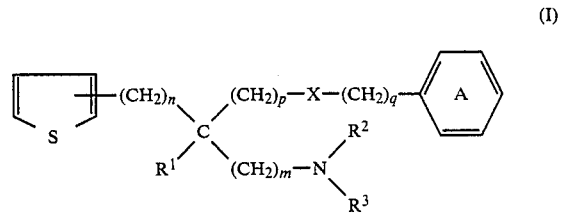

(I)

wherein $R^1$, and $R^2$ and $R^3$ are a lower alkyl group, Ring A is phenyl, a lower alkylenedioxy-substituted phenyl, a phenyl group having 1 to 3 substituent(s) selected from the group consisting of a lower alkyl group, a lower alkylthio group, a lower alkoxy group, a phenyl-lower alkoxy group, a lower alkoxycarbonyl group, a halogen atom, amino group and hydroxy group, X is —OCO—, —O— or —S—, m and n are an integer of zero or 1, and p and q are an integer of zero, 1 or 2, or a salt thereof.

8 Claims, No Drawings

THIOPHENE DERIVATIVE AND PROCESS FOR PREPARING THE SAME

This invention relates to a novel thiophene derivative and processes for preparing the same. More particularly, it relates to a novel thiophene derivative of the formula:

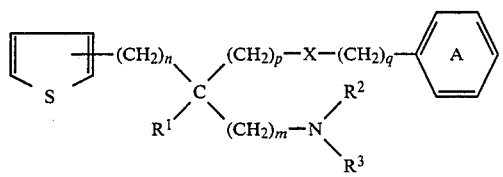
(I)

wherein $R_1$, $R^2$ and $R_3$ are a lower alkyl group, Ring A is a substituted or unsubstituted phenyl group, X is —OCO—, —O—or —S—, m and n are an integer of zero or 1 and p and q are an integer of zero, 1 or 2, or a salt thereof.

It is known that trimebutine maleate (chemical name: 2-dimethylamino-2-phenylbutyl 3,4,5-trimethoxybenzoate maleate) is useful as a regulator of gastrointestinal tract motility [cf. Japan. J. Pharmacol. Vol. 34, pp 177-181 (1984)].

As a result of various investigations, we have now found that the thiophene derivative (I) or a salt thereof has a potent regulating effect on the motility of the gastrointestinal tract.

Representative examples of the compound of the present invention include those of the formula (I) in which $R^1$, $R^2$ and $R_3$ are a lower alkyl group such as methyl, ethyl, propyl or butyl; Ring A is phenyl, a lower alkylenedioxy-substituted phenyl, a phenyl group having 1 to 3 substituent(s) selected from the group consisting of a lower alkyl group (e.g., methyl, ethyl, propyl, butyl), a lower alkylthio group (e.g., methylthio, ethylthio, propylthio, butylthio), a lower alkoxy group (e.g., methoxy, ethoxy, propoxy, butoxy), a phenyl-lower alkoxy group (e.g., benzyloxy, phenethyloxy, phenylpropyloxy, phenylbutyloxy), a lower alkoxycarbonyl group (e.g., methoxycarbonyl, ethoxycarbonyl, propoxycarbonyl, butoxycarbonyl), a halogen atom (e.g., fluorine, chlorine, bromine), amino group and hydroxy group; X is —OCO—, —O— or —S—; m and n are an integer of zero or 1; and p and q are an integer of zero, 1 or 2.

Among them, a preferred subgenus includes those of the formula (I) in which, $R^1$, $R^2$ and $R^3$ are methyl or ethyl; Ring A is phenyl, methylenedioxy-substituted phenyl, or phenyl having 1 to 3 substituent(s) selected from the group consisting of methyl, n-propyl, tert.-butyl, methylthio, methoxy, benzyloxy, methoxycarbonyl, chlorine, amino and hydroxy; X is —OCO—, —O— or —S—; m and n are an integer of zero or 1; and p and q are an integer of zero, 1 or 2.

The more preferred subgenus includes those of the formula (I) in which $R^1$, $R^2$ and $R_3$ are methyl or ethyl; Ring A is phenyl, 3,4-methylenedioxyphenyl, 4-methylphenyl, 4-methylthiophenyl, 3-methoxyphenyl, 4-methoxyphenyl, 2,4-dimethoxyphenyl, 3,4-dimethoxyphenyl, 2,3,4-trimethoxyphenyl, 3,4,5-trimethoxyphenyl, 2-benzyloxy-3-methoxyphenyl, 2-methoxy-5-methoxycarbonylphenyl, 3-methoxy-2-n-propylphenyl, 3,5-ditert.-butyl-4-hydroxyphenyl, 4-hydroxy-3,5-dimethoxyphenyl, 4-chlorophenyl, 2-chloro-5-methoxyphenyl, 4-chloro-3-methoxyphenyl, 5-chloro-2-methoxyphenyl or 4-amino-3-chloro-2-methoxyphenyl; X is —OCO—, —O— or —S—; m and n are zero or 1; and p and q are zero, 1 or 2.

Further the preferred subgenus includes those of the formula (I) in which $R^1$ is ethyl, $R^2$ and $R_3$ are methyl, Ring A is phenyl, 3,4,5-trimethoxyphenyl or 4-hydroxy-3,5-dimethoxyphenyl, X is —OCO—, —O— or —S—, n and m are zero or 1, and p and q are zero, 1 or 2.

Still further preferred subgenus includes those of the formula (I) in which $R^1$ is ethyl, $R^2$ and $R^3$ are methyl, Ring A is 3,4,5-trimethoxyphenyl or 4-hydroxy-3,5-dimethoxyphenyl, X is —OCO—, —O— or —S—, n and m are zero or 1, p is 1 or 2, and q is zero or 1.

While the compound (I) of the present invention can exist in the form of optical isomers due to the asymmetric carbon atom involved therein, the present invention includes both of such optical isomers and a racemic modification thereof.

The compound (I) of the present invention can be prepared, for example, by (A) alkylating an amine compound of the

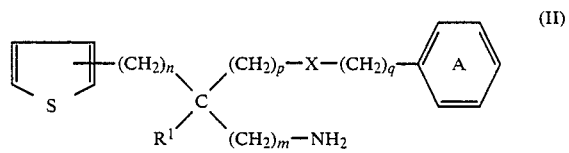
(II)

wherein $R^1$, Ring A, X, n, m, p and q are the same as defined above.

The compound (I) in which X is a group of the formula: —OCO—can also be prepared by (B) condensing an aminoalkanol compound of the formula:

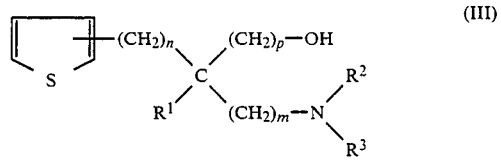
(III)

wherein $R^1$, $R^2$, $R_3$, n, m and p are the same as defined above, with a carboxylic acid compound of the formula:

(IV)

wherein Ring A and q are the same as defined above, or a reactive derivative thereof.

Alternatively, the compound (I) in which X is a group of the formula: —O— can be prepared by (C) reacting the aminoalkanol compound (III) with a compound of the formula:

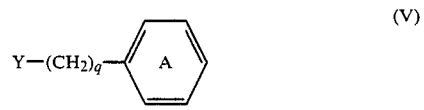
(V)

wherein Y is a reactive residue and Ring A and q are the same as defined above.

Method (A)

The alkylation of the amine compound (II) can be accomplished by reacting the compound (II) with an aldehyde compound of the formula: R—CHO (wherein R is hydrogen atom or a lower alkyl group of a less number of carbon atoms than that of $R^2$ (or $R_3$) by one carbon atom) in the presence of a reducing agent. The reducing agent includes, for example, sodium cyanoborohydride, sodium borohydride, formic acid, sodium formate and the like. It is preferred to carry out the reaction in a suitable solvent (e.g., alkanol, acetonitrile) or without solvent at a temperature of −5° to 120° C.

The alkylation of the amine compound (II) can be also be carried out by reacting the compound (II) with a lower alkyl halide (e.g., methyl iodide, ethyl iodide) in the presence of an acid acceptor (e.g., potassium carbonate, sodium bicarbonate). It is preferred to carry out the reaction in a suitable solvent (e.g., dimethylsulfoxide, hexamethylphosphoric triamide, ethyl acetate) at a temperature of 0° to 90° C.

Method (B)

The condensation reaction of the aminoalkanol compound (III) with the carboxylic acid compound (IV) or a reactive derivative thereof can be conducted in a conventional manner. For example, the condensation reaction of the compound (III) with the carboxylic acid compound (IV) in its free form can be conducted in the presence of a dehydrating agent (e.g., carbonyldiimidazole, dicyclohexylcarbodiimide) in a solvent (e.g., tetrahydrofuran, chloroform). It is preferred to carry out the reaction at a temperature of −10° to 50° C.

The condensation reaction of the compound (III) with the reactive derivative of the carboxylic acid (IV) can be conducted either in the presence or absence of an acid acceptor in a solvent. Suitable examples of the reactive derivative of the carboxylic acid (IV) include the corresponding acid halides (e.g., acid chloride, acid bromide), anhydride, mixed anhydrides (e.g., a mixed anhydride of the carboxylic acid compound (IV) with an alkyl carbonate) and active esters (e.g., p-nitrophenyl ester, 2,4-dinitrophenyl ester, succinimide ester, phthalimide ester, benzotriazole ester). Suitable examples of the acid acceptor include trialkylamines (e.g., trimethylamine, triethylamine), pyridine, alkali metal carbonates (sodium carbonate, potassium carbonate) and alkali metal bicarbonates (e.g., sodium bicarbonates, potassium bicarbonate). It is preferred to carry out the reaction in a suitable solvent (e.g., tetrahydrofuran, chloroform, methylene chloride, acetonitrile, toluene, N,N-dimethylformamide) at a temperature of −20° to 100° C.

A lower alkyl ester (e.g., methyl ester) of the compound (IV) can also be employed as the reactive derivative of the compound (IV). In this case, it is preferred to carry out the condensation reaction in a suitable solvent (e.g., toluene, benzene) in the presence of a catalyst (e.g., alkali metal alkoxide) at a temperature of 10° to 130° C.

Method (C)

The reaction of the aminoalkanol compound (III) with the compound (V) can be carried out in the presence of an acid acceptor. Examples of the reactive residue represented by Y in the compound (V) include, for example, a halogen atom such as chlorine, bromine or iodine, an alkylsulfonyloxy group such as methanesulfonyloxy and an arylsulfonyloxy group such as p-toluenesulfonyloxy group. Suitable examples of the acid acceptor include alkali metal hydroxides (e.g., sodium hydroxide, potassium hydroxide), alkali metal hydride (e.g., sodium hydride) and alkali metal alkoxides (e.g., sodium methoxide, sodium ethoxide). It is preferred to carry out the reaction in a suitable solvent (e.g., tetrahydrofuran, dioxane, dimethylsulfoxide, toluene) at a temperature of 0° to 50° C.

When the thus-obtained compound (I) is the compound (I) in which Ring A is 3,4,5-tri(lower alkoxy)phenyl group, if required, said compound may be subjected to dealkylation reaction to give the compound (I) in which Ring A is 4-hydroxy-3,5-di(lower alkoxy) phenyl group. The dealkylation can be conducted by treating the trialkoxyphenyl-compound (I) with thiocresol, sodium hydride or hexamethylphosphoric triamide. It is preferred to carry out the reaction in a suitable solvent (e.g., toluene, xylene) at a temperature of 20° to 150° C.

When the compound (I) is obtained in the form of a racemic modification, it may be resolved into each optical isomer by a conventional manner. For example, the optical resolution can be carried out by reacting the racemic modification of the compound (I) with a resolving agent (e.g., optically active tartaric acid, d-camphorsulfonic acid) in a solvent (e.g., lower alkanol), isolating the crystals of a less soluble diastereoisomeric salt by utilizing the difference in solubility of two diastereoisomeric salts and further isolating the more soluble diastereoisomeric salt from the mother liquor. The diastereoisomeric salts thus obtained can be converted to the desired optically active compound (I), for example, by treating with an alkali (e.g., alkali metal hydroxide, alkali metal carbonate).

The compound (I) of the present invention can be used as a medicament either in the free form or in the form of a pharmaceutically acceptable salt thereof. The pharmaceutically acceptable salt includes, for example, inorganic acid addition salts such as hydrochloride, hydrobromide, sulfate or phosphate; and organic acid addition salts such as succinate, maleate, fumarate or tartarate. These salts can easily be prepared by treating the compound (I) with the corresponding acid according to a conventional manner.

As mentioned hereinbefore, the compound (I) and its salts have a potent regulating effect on the motility of gastrointestinal tracts and especially are characterized by a potent excitatory effect on the gastrointestinal tracts in conditions of depressed activity. Moreover, the compound (I) in which X is —OCO— or —S— is characterized in that it shows dual effects on the gastrointestinal motility, i.e., excitatory effect on the gastrointestinal tracts in conditions of depressed activity and inhibitory effect on the gastrointestinal tracts in conditions of hyperactivity. Further, the compound (I) and its salts are also characterized in that they are low in toxity and therefore have great safety as a medicament. Therefore, the compound (I) and its salts are useful as the regulator of gastrointestinal tract motility in warm-blooded animals including human being. For example, they can be used for the improvement, treatment and/or prophylaxis of gastrointestinal symptoms (e.g., abdominal pain, nausea, abdominal distension) in chronic gastritis, irritable bowel syndrome and the like.

The compound (I) and its salts may be administered orally or parenterally (e.g., intravenously, intramuscularly, intradermally). The dose of the compound (I) and a pharmaceutically acceptable salt thereof may vary depending on the administration route, the age, weight and condition of patients, severity of diseases, and the like, but is usually in the range of about 0.001 to 50 mg/kg/day. In case of oral administration, said dose is especially in the range of about 1 to 20 mg/kg/day.

The compound (I) and its salts may be used in the form of a pharmaceutical preparation containing the same compound in conjunction or admixture with pharmaceutical excipients suitable for oral or parenteral administration. The pharmaceutical preparation may be in solid form such as tablets, granules or capsules; or in liquid form such as solutions, suspensions or emulsions. They may be sterilized and/or may further contain auxiliaries such as stabilizing, wetting or emulsifying agent.

The starting compound (II) of the present invention can be prepared, for example, by hydrolyzing a compound of the formula:

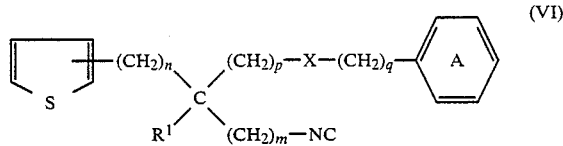

(VI)

wherein the symbols are the same as defined above, with an acid (e.g., hydrochloric acid). The starting compound (III) can be prepared, for example, by alkylating a compound of the formula:

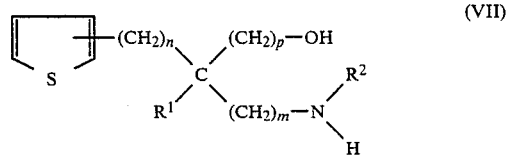

(VII)

wherein the symbols are the same as defined above, in the same manner as described in the alkylation of the compound (II). Moreover, the compound (III) in which p is 1 or 2 can be prepared by treating a compound of the formula:

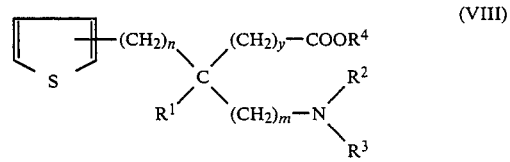

(VIII)

wherein $R^4$ is a lower alkyl group, y is an integer of zero or 1, and $R^1$ to $R^3$, m and n are the same as defined above, with a reducing agent (e.g., lithium aluminum hydride). Further, the compound (III) in which p is zero can be prepared by reacting a compound of the formula:

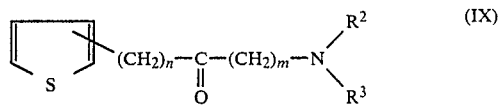

(IX)

wherein the symbols are the same as defined above, with Grignard reagent of the formula: $R^1MgI$ (wherein $R^1$ is the same as defined above). When the starting compound (II) or (III) is obtained in the form of a racemic mixture, if required, it may be resolved into each optical isomer by a conventional manner.

Throughout the specification and claims, the term "lower alkyl", "lower alkoxy" and "lower alkylene" should be interpreted as referring to alkyl having one to four carbon atoms, alkoxy having one to four carbon atoms and alkylene having one to two carbon atoms, respectively.

Experiments

Effect on the motility of the stomach and colon in anesthetized rat (Method)

Male rats (11 to 18 weeks old, body weight: 310–460 g) which were fasted for 20 hours were anesthetized with urethane and α-chloralose (s.c.). After the laparotomy, a force-transducer for measuring the gastrointestinal motility was attached to the gastric body and proximal colon (7 to 10 cm from the ileoceal sphincter) of the rats, and the gastric and colonic motility was recorded on a recorder through an amplifier. A test compound (dose: 1 mg/kg) dissolved in a physiological saline solution or suspended in a 0.25% carboxymethylcellulose solution was injected in the femoral vein.

Excitatory or inhibitory effect (E) of the test compound was expressed as a value relative to that of the contraction produced by bethanechol chloride (10 μg/kg, i.v.) or to that of the relaxation produced by isoproterenol hydrochloride (30 μg/kg, i.v.) which is taken as 1.0, respectively. Then, the effect of the test compound on the motility of the stomach and colon was judged according to the criteria mentioned below.

(Criteria)

| Effect (E) | Judgment |
|---|---|
| E ≧ 1.30 | ++++ |
| 1.30 > E > 0.70 | +++ |
| 0.70 > E ≧ 0.40 | ++ |
| 0.40 > E ≧ 0.10 | + |
| E < 0.10 | − |

(Test Compound)

The test compounds used in the experiments are shown in Table 1.

TABLE 1

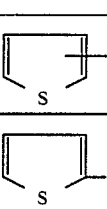

(A)

| Nos. |  | n | m | p | q | X | A |
|---|---|---|---|---|---|---|---|
| 1 | 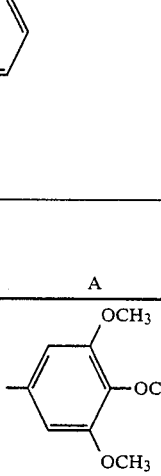 | 0 | 0 | 1 | 0 | 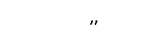 |  |
| 2 | " | " | " | " | 2 | " | —S— | " |
| 3 | " | " | " | " | 1 | 1 | —O— | 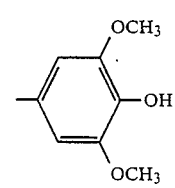 |
| 4 | 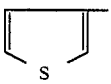 | " | " | " | 0 |  | 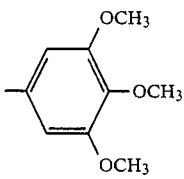 |
| 5 |  | 1 | " | " | 1 | —O— | " |

(Results)
The results are shown in Tables 2 and 3.

TABLE 2

| Compound Nos. | Excitatory effect of rat colon |
|---|---|
| 1 | +++ |
| 2 | +++ |
| 3 | +++ |
| 4 | ++++ |
| 5 | ++++ |

TABLE 3

| Compound Nos. | rat stomach Inhibitory effect | Excitatory effect |
|---|---|---|
| 1 | ++ | ++ |
| 2 | +++ | ++ |

Note: Compound Nos. 1 and 2 produced a biphasic response, i.e., relaxation followed by contraction.

EXAMPLE 1

(1) A solution of methyl 2-dimethylamino-2-(2-thienyl)butyrate (11.4 g) in tetrahydrofuran (50 ml) is added dropwise to a suspension of lithium aluminum hydride (1.6 g) in tetrahydrofuran (50 ml) under ice-cooling. The mixture is stirred at room temperature for 2 hours, and water (1.6 ml), an aqueous 15% sodium hydroxide solution (1.6 ml) and water (4.8 ml) are added to the mixture, successively. After the mixture is stirred, insoluble materials are filtered off, and the filtrate is concentrated under reduced pressure to remove solvent. The residue is distilled under reduced pressure, whereby 2-dimethylamino-2-(2-thienyl)-1-butanol (9.1 g) is obtained as colorless crystals. Yield: 91%
m.p. 66°–68° C.
IR$\nu_{max}^{Nujol}$(cm$^{-1}$): 3400, 3100.
NMR(CDCl$_3$)δ: 0.82(3H, t), 2.94(2H, q), 2.16(6H, s), 2.81 (1H, broad s), 3.68, 3.94(2H, ABq, J$_{AB}$=10 Hz), 6.7–7.2(3H, m).

(2) 2-Dimethylamino-2-(2-thienyl)-1-butanol (8 g), triethylamine (4.85 g) and dimethylaminopyridine (catalytic amount) are dissolved in tetrahydrofuran (10 ml), and 3,4,5-trimethoxybenzoyl chloride (11.1 g) is gradually added to the solution under ice-cooling. The mixture is stirred at room temperature for 16 hours and concentrated under reduced pressure to remove solvent. The residue is dissolved in diluted hydrochloric acid, and the solution is washed with ether. The solution is alkalized with potassium carbonate and extracted with ethyl acetate. The extract is washed with an aqueous saturated sodium chloride solution, dried and then concentrated under reduced pressure to remove solvent. The residue is purified by silica gel column chromatography (solvent, n-hexane:ethyl acetate=5:2), whereby 2-dimethylamino-2-(2-thienyl)-butyl 3,4,5-trimethoxybenzoate (12.8 g) is obtained as colorless oil.

Yield: 81.3%.

IR$\nu_{max}^{film}$(cm$^{-1}$): 1720, 1590.

MS(m/e): 364 (M$^+$—H$_5$).

NMR(CDCl$_3$)δ: 0.87(3H, t), 1.8–2.2(2H, m), 2.4(6H, s), 3.87, 3.9(9H, ss), 4.73(2H, s), 6.9–7.05, 7.18–7.4(3H, m).

Hydrochloride of the product:
m.p. 164°–165° C.
IR$\nu_{max}^{Nujol}$(cm$^{-1}$): 1720, 1585.
Maleate of the product:
m.p. 107°–109° C.

Examples 2 to 10

2-Dimethylamino-2-(2-thienyl)-1-butanol and substituted benzoyl chloride (or substituted benzylcarbonyl chloride) are treated in the same manner as described in Example 1-(2), whereby the compounds shown in the following Table 4 are obtained.

TABLE 4

(I-a)

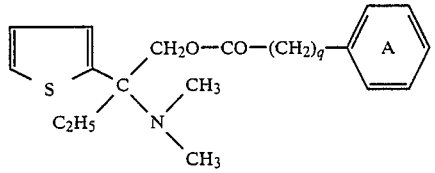

| Example Nos. | Compound (I-a) Ring A | q | Properties |
|---|---|---|---|
| 2 | —⟨⟩—OCH$_3$ | 0 | Yield: 60% colorless oil Hydrochloride: colorless crystals m.p. 182–183° C. IR$\nu_{max}^{KBr}$(cm$^{-1}$): 1705, 1600 MS(m/e): 304 (M$^+$—C$_2$H$_5$, HCl) |
| 3 | OCH$_3$ / —⟨⟩—OCH$_3$ | 0 | Yield: 71.2% colorless oil IR$\nu_{max}^{film}$(cm$^{-1}$): 1720, 1600 MS(m/e): 363 (M$^+$) Hydrochloride: colorless crystals m.p. 175–177° C. |
| 4 | OCH$_3$ —⟨⟩—OCH$_3$ | 0 | Yield: 88% colorless oil IR$\nu_{max}^{film}$(cm$^{-1}$): 1710, 1600 MS(m/e): 363 (M$^+$) Hydrochloride: colorless crystals m.p. 178–179° C. |
| 5 | —⟨⟩—OCH$_3$ OCH$_3$ OCH$_3$ | 0 | Yield: 63.3% colorless oil IR$\nu_{max}^{film}$(cm$^{-1}$): 1720, 1600 MS(m/e): 393 (M$^+$) Hydrochloride: colorless crystals m.p. 153–154° C. |
| 6 | —⟨⟩—O\\CH$_2$/O | 0 | Yield: 69% colorless oil IR$\nu_{max}^{film}$(cm$^{-1}$): 1710, 1600 MS(m/e): 318 (M$^+$—C$_2$H$_5$) |
| 7 | —⟨⟩—Cl | 0 | Yield: 76% colorless oil IR$\nu_{max}^{film}$(cm$^{-1}$): 1720, 1600 MS(m/e): 308 (M$^+$—C$_2$H$_5$) Hydrochloride: colorless crystals m.p. 183–184° C. |
| 8 | —⟨⟩—CH$_3$ | 0 | Yield: 76% colorless oil IR$\nu_{max}^{film}$(cm$^{-1}$): 1710, 1610 MS(cm$^{-1}$): 288 (M$^+$—C$_2$H$_5$) |

TABLE 4-continued $$\text{(I-a)}$$

Structure (I-a): 2-thienyl-C(C₂H₅)(N(CH₃)₂)-CH₂O-CO-(CH₂)_q-A

| Example Nos. | Ring A | q | Properties |
|---|---|---|---|
| 9 | 2,3,4-trimethoxyphenyl (OCH₃, OCH₃, OCH₃) | 1 | Yield: 51% colorless oil IR$\nu_{max}^{film}$(cm$^{-1}$): 1740, MS(m/e): 378 (M$^+$—C₂H₅) |
| 10 | phenyl | 0 | Yield: 72.3% colorless oil IR$\nu_{max}^{film}$(cm$^{-1}$): 1700, 1600 MS(m/e): 258 (M$^+$—N(CH₃)₂ + H) Hydrochloride: colorless crystals m.p. 169–170° C. |

EXAMPLE 11

(1) Methyl 2-diethyamino-2-(2-thienyl)butyrate (9.23 g) is treated in the same manner as described in Example 1-(1), whereby 2-diethylamino-2-(2-thienyl)-1-butanol (8.07 g) is obtained as colorless oil.

IR$\nu_{max}^{Nujol}$(cm$^{-1}$): 3400.

MS(m/e): 198 (M$^+$—C₂H₅).

NMR(CDCl₃)δ: 0.78(3H, t), 1.05(6H, t), 1.95(2H, q), 2.59 (4H, q), 3.03(1H, s), 3.75(2H, s), 6.75–7.27(3H, m)

(2) The product (2.0 g) obtained in Paragraph (1) and 3,4,5-trimethoxybenzoyl chloride (2.24 g) are treated in the same manner as Example 1-(2), whereby 2-diethylamino-2-(2-thienyl)butyl 3,4,5-trimethoxybenzoate (2.35 g) is obtained as colorless crystals. Yield: 63.3%

IR$\nu_{max}^{film}$ cm$^{-1}$): 1715, 1590.

MS(m/e): 392 (M$^+$—C₂H₅).

NMR(CDCl₃)δ: 0.83(3H, t), 1.1(6H, t), 1.75–2.3(2H, m), 2.5–3.1(4H, m), 3.8–4.05(9H, m), 4.68(2H, s), 6.86–7.0(2H, m), 7.15–7.4(3H, m).

Hydrochloride of the product:

m.p. 125°–127° C. (recrystallized from ethanol-ether).

EXAMPLE 12

(1) Ethyl 2-dimethylamino-2-(2-thienyl)propionate 0.88 g) is treated in the same manner as described in Example 1-(1), whereby 2-dimethylamino-2-(2-thienyl)-1-propanol (0.49 g) is obtained as colorless crystals.

m.p. 68°–70° C.

IR$\nu_{max}^{Nujol}$ (cm$^{-1}$): 3050.

MS(m/e): 185 (M$^+$).

NMR(CDCl₃)δ: 1.46(3H, s), 2.2(6H, s), 3.71(2H, dd, J=10.5, 18Hz), 6.85–7.33(3H, m). (2) The product (2 g) obtained in Paragraph (1) and 3,4,5-trimethoxybenzoyl chloride (2.74 g) are treated in the same manner as described in Example 1-(2), whereby 2-dimethylamino-2-(2-thienyl)propyl 3,4,5-trimethoxybenzoate (3.16 g) are obtained as colorless crystals. Yield: 77.1%

IR$\nu_{max}^{KBr}$(cm$^{-1}$): 1708, 1590.

Ms(m/e): 379 (M$^+$—C₂H₅).

NMR(CDCl₃)δ: 1.52(3H, s), 2.33(6H, s), 3.8–4.0(9H, m) 4.49(2H, s), 6.85–7.05(2H, m), 7.18–7.35(3H, m).

Hydrochloride of the product:

m.p. 132°–135° C. (recrystallized from ethanol-ether).

EXAMPLE 13

(1) Ethyl 2-dimethylamino-2-(3-thienyl)butyrate (7.1 g) is treated in the same manner as described in Example 1-(1), whereby 2-dimethylamino-2-(3-thienyl)-1-butanol (5.8 g) is obtained as an oil.

Yield: 98.9%.

IR$\nu_{max}^{film}$(cm$^{-1}$): 3400.

MS(m/e): 168 (M$^+$—C₂H₅).

NMRN(CDCl₃)δ: 0.78(3H, t), 1.72–2.12(2H, m), 2.18(6H, s), 3.03(1H, broad s), 3.66, 3.95(2H, AB, J=10 Hz), 6.9–7.3(3H, m).

(2) The product (2 g) obtained in Paragraph (1) and 3,4,5-trimethoxybenzoyl chloride (3.5 g) is treated in the same manner as described in Example 1-(2), whereby 2-dimethylamino-2-(3-thienyl)butyl 3,4,5-trimethoxybenzoate (2.3 g) is obtained a pale yellow oil.

Yield: 59.2%.

IR$\nu_{max}^{film}$ 1710.

MS(m/e): 364 (M$^+$—C₂H₅)

NMR(CDCl₃)δ: 0.79(3H, t), 1.78–2.13(2H, m), 2.33(6H,s), 3.80, 3.83(9H, ss), 4.68(2H, s), 6.98–7.28(5H,m).

EXAMPLE 14

(1) A solution of dimethylamine (5.3 g) in ether (50 ml) is cooled to −15° C. and a solution of 2-chloroacetylthiophene (12.5 g) in ether (60 ml) is added dropwise to the solution at a temperature below −10° C. The mixture is stirred at the same temperature for 2 days, alkalized with an aqueous sodium bicarbonate solution and then extracted with ether. The extract is washed with an aqueous saturated sodium chloride solution, dried and concentrated to remove solvent. The residue is purified by silica gel column chromatography aminoacetyl-thiophene (10.5 g ) is obtained as pale yellow oil.

Yield: 80%.
IR$\nu_{max}^{film}$(cm$^{-1}$): 1660.
MS(m/e): 169 (M+).

(2) A solution of ethyl iodide (24.2 g) in ether (100 ml) is added dropwise to a suspension of metalic magnesium (3.77 g) in ether (200 ml), and the mixture is stirred at room temperature for 30 minutes. A solution of 2-dimethylaminoacetylthiophene (10.5 g) in ether (40 ml) is added dropwise to the mixture at room temperature with stirring, and the mixture is further stirred at the same temperature for 16 hours. An aqueous 10% ammonium chloride solution is added to the mixture and the organic layer is collected therefrom. The organic layer is washed with an aqueous saturated sodium chloride solution, dried and then concentrated to remove solvent. The residue is purified by alumina column chromatography (solvent, n-hexane : ethyl acetate=40 : 1), whereby 1-dimethyl-aminomethyl-1-(2-thienyl)-1-propanol (6.3 g) is obtained as pale yellow oil.
Yield: 51%.
IR$\nu_{max}^{film}$(cm$^{-1}$): 3400.
NMR(CDCl$_3$)$\delta$: 0.81(3H, t), 1.72(2H, q), 2.12, (6H, s), 2.62(2H, s), 4.03–4.49(1H, braod), 6.65–7.15(3H, m).

(3) The product (1 g) obtained in Paragraph (2) and 3,4,5-trimethoxybenzoyl chloride (1.73 g) are treated in the same manner as described in Example 1-(2), whereby 1-dimethylamino- 1-(2-thienyl)propyl 3,4,5-trimethoxybenzoate (1.43 g) is obtained as pale yellow oil.
Yield: 72.7%.
IR$\nu_{max}^{film}$(cm$^{-1}$): 1750, 1590.
NMR(CDCl$_3$)$\delta$: 0.75(3H, t), 2.12(6H, s , 2.1–3.0(4H, m), 3.83(9H, s), 6.40(2H, s), 6.85–7.30(3H, m).
Hydrochloride of the product:
m.p. 123°–125° C. (recrystallized from methylene chloridediisopropyl ether).

EXAMPLE 15

1-Dimethylaminomethyl-1-(2-thienyl)-1-propanol (1.12 g) and 3-(3,4,5-trimethoxyphenyl)propionyl chloride (1.61 g) are treated in the same manner as described in Example 1-(2), whereby 1-dimethylaminomethyl-1-(2-thienyl)propyl 3-(3,4,5-trimethoxyphenyl)propionate (1.23 g) is obtained as colorless oil.
Yield: 51.9%.
IR$\nu_{max}^{film}$ (cm$^{-1}$): 1735, 1590.
NMR(CDCl$_3$)$\delta$: 0.75(3H, t), 2.12(6H, s), 2.33(2H, q), 2.6–3.0(4H, m), 3.0(2H, s), 3.82(9H,s), 6.4(2H, s), 6.85–7.3(3H, m).
Hydrochloride of the product:
m.p. 130° C. (recrystallized from methylene chloride diisopropyl ether)

EXAMPLE 16

(1) A suspension of potassium tert.-butoxide (5.5 g) in tetrahydrofuran (50 ml) is cooled to −30° C., and a solution of methyl 2-isocyanobutyrate (5.5 g) in tetrahydrofuran (10 ml) is added dropwise to the suspension at −30° C. The mixture is stirred at the same temperature for 30 minutes and a solution of 2-bromomethylthiophene (6.9 g) in tetrahydrafuran (10 ml) is added dropwise to the mixture. The mixture is stirred at room temperature for 4 hours, adjusted to pH 7 with acetic acid and then concentrated under reduced pressure to remove solvent. The residue is dissolved in a mixture of ethyl acetate and water and the organic layer is collected therefrom. The organic layer is washed with an aqueous saturated sodium chloride solution, dried and concentrated to remove solvent. The residue is distilled under reduced pressure, whereby methyl 2-isocyano-2-(2-thienylmethyl)butyrate (7.7 g) is obtained as pale yellow oil.
Yield 79.7%.
b.p. 140° C./5 mmHg.
IR$_{max}^{film}$(cm$^{-1}$): 2100, 1740.

(2) A solution of the product (7.7 g) in tetrahydrofuran (40 ml) is added dropwise to a suspension of lithium aluminum hydride (2 g) in tetrahydrofuran (20 ml) under ice-cooling and the mixture is stirred at room temperature overnight. Water (2 ml), an aqueous 15% sodium hydroxide solution (2 ml) and water (2 ml) are added to the mixture, successively. After the mixture is stirred, the mixture is filtered and the filtrate is concentrated under reduced pressure to remove solvent, whereby 2-methylamino-2-(2-thienylmethyl)-1-butanol (3.9 g) is obtained as pale yellow oil.
Yield: 56.7%.
IR$\nu_{max}^{film}$(cm$^{-1}$): 3350.

(3) 35% Formalin (1.3 ml) and formic acid (1.2 ml) are added to the product (2.2 g) obtained in Paragraph (2) and the mixture is stirred at 105° C. for one hour. After cooling, the mixture is alkalized with an aqueous potassium carbonate solution and extracted with ethyl acetate. The extract is washed with an aqueous saturated sodium chloride solution, dried and concentrated to remove solvent, whereby 2-dimethylamino-2-(2-thienylmethyl)-1-butanol (2 g) is obtained. Yield: 85.0%.
IR$\nu_{max}^{film}$: 3400.
NMR(CDCl$_3$)$\delta$: 0.94(3H, t), 1.38–1.72(2H, m), 2.38(6H, s), 2.64–3.07 (1H, broad s), 2.90(2H, s), 3.37(2H, s), 6.67–7.08(3H, m).

(4) The product (2 g) obtained in Paragraph (3) is dissolved in dimethylsulfoxide (2.4 ml) and powdery potassium hydroxide (2.6 g) is added to the solution. 3,4,5-Trimethoxybenzyl chloride (2 g) is added to the mixture and the mixture is stirred at room temperature for one hour. The mixture is acidified with 10% hydrochloric acid under ice-cooling and washed with ether. The aqueous layer is adjusted to pH 10 with potassium carbonate and extracted with ether. The extract is washed with an aqueous saturated sodium chloride solution, dried and concentrated to remove solvent. The residue is purified by silica gel column chromatography (solvent, chloroform : ethanol=10 : 1), whereby 1-(3,4,5-trimethoxybenzyloxymethyl)-1-(2-thienylmethyl)-N,N-dimethylpropylamine (2.2 g) is obtained as pale yellow oil.
Yield: 59.6%.
IR$\nu_{max}^{film}$(cm$^{-1}$): 1590.
NMR(CDCl$_3$)$\delta$: 0.88(3H, t), 1.34–1.66(2H, m), 2.39(6H, s), 2.85, 3.20(2H, ABq, J$_{AB}$=14 Hz), 3.30, 3.45(2H, AB$_q$, J$_{AB}$=9 Hz), 3.78(9H, s), 4.37(2H, s), 6.48(2H, s), 6.6–7.1 (3H, m).

EXAMPLES 17 to 29

2-Dimethylamino-2-(2-thienyl)-1-butanol and substituted-benzyl chloride are treated in the same manner as described in Example 16-(4), whereby the compounds shown in the following Table 5 are obtained.

TABLE 5

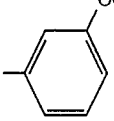

| Example Nos. | Ring A | Properties |
|---|---|---|
| 17 | 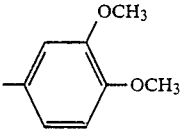 | Yield: 84.2%<br>colorless oil<br>IR$\nu_{max}^{film}$(cm$^{-1}$): 1600<br>MS(m/e): 319 (M$^+$)<br>Maleate:<br>m.p. 86–87° C. (ethanol) |
| 18 | 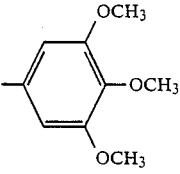 | Yield: 74.2%<br>colorless oil<br>IR$\nu_{max}^{film}$(cm$^{-1}$): 1600<br>MS(m/e): 349 (M$^+$) |
| 19 | 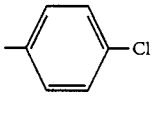 | Yield: 84.7%<br>colorless oil<br>IR$\nu_{max}^{film}$(cm$^{-1}$): 1590<br>MS(m/e): 379 (M$^+$)<br>Maleate:<br>colorless crystals<br>m.p. 110–112° C. (ethyl acetate) |
| 20 | 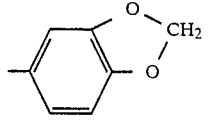 | Yield: 53.3%<br>colorless oil<br>MS(m/e): 323 (M$^+$)<br>Maleate:<br>colorless needles<br>m.p. 134–136° C. (ethyl acetate) |
| 21 | 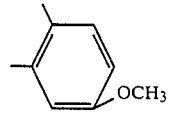 | Yield: 75.1%<br>colorless oil<br>MS(m/e): 333 (M$^+$)<br>Maleate:<br>colorless needles<br>m.p. 130–131° C. (ethyl acetate) |
| 22 | 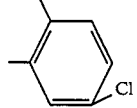 | Yield: 54%<br>½ 1,5-naphthalenedisulfonate:<br>m.p. 173–176° C. (dec.) |
| 23 | 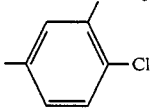 | Yield: 56%<br>Maleate:<br>m.p. 122–124° C. |
| 24 |  | Yield: 54%<br>Maleate:<br>m.p. 120–122° C. |

TABLE 5-continued (I-b)

[Structure: thiophene ring-S, with central C bearing C2H5, CH2-O-CH2-A (ring A), and N(CH3)2]

| Example Nos. | Compound (I-b) Ring A | Properties |
|---|---|---|
| 25 | [benzyl with OCH2- attachment and OCH3 substituent on attached phenyl] | Yield: 62.5%<br>½ 1,5-Naphthalenedisulfonate:<br>m.p. 96–99°C. |
| 26 | [phenyl with OCH3 and COOCH3] | Maleate:<br>m.p. 88–90°C. |
| 27 | [phenyl with SCH3] | Yield: 59%<br>Maleate:<br>m.p. 96–98°C. |
| 28 | [phenyl with C3H7 and OCH3] | Yield: 72.2%<br>NMR(CDCl$_3$)δ: 0.77(3H, t), 0.96 (3H, t), 1.35–1.80(2H, m), 1.8–2.1(2H, m), 2.28(6H, s), 2.76 (2H, t), 3.77(3H, s), 3.75, 3.86 (2H, AB$_q$), 4.57(2H, s), 6.7–7.2 (6H, m) |
| 29 | [phenyl with two C(CH3)3 and OH] | Yield: 71.4%<br>Maleate:<br>m.p. 132–133°C. |

EXAMPLE 30

(1) 15% Hydrogen chloride/methanol solution (12 ml) is added to 1-ethyl-3-(3,4,5-trimethoxyphenylthio)-1-(2-thienyl)propyl isocyanide (2.3 g) under ice-cooling and the mixture is stirred at room temperature for 3 hours. The mixture is concentrated under reduced pressure to remove solvent and the residue is adjusted to pH 10 with an aqueous potassium carbonate solution. The aqueous mixture is extracted with ethyl acetate and the extract is washed with an aqueous saturated sodium chloride solution, dried and then concentrated to remove solvent. The residue is purified by silica gel column chromatography (solvent, n-hexane:ethyl acetate=4:1), whereby 1-ethyl-3-(3,4,5-trimethoxyphenylthio)-1-(2-thienyl)propylamine (1.9 g) is obtained as colorless oil.

Yield: 84.9%.

IR$_{max}^{film}$(cm$^{-1}$): 3400, 3300.

MS(m/e): 367 (M$^+$).

NMR(CDCl$_3$)δ: 0.79(3H, t), 1.57(2H, s), 2.62–2.96 (2H, m), 3.72(9H, s), 6.39(2H, s), 6.61–6.87, 6.97–7.09(3H, m).

(2). The product (3.9 g) obtained in Paragraph (1) is dissolved in acetonitrile (30 ml), and 35% formalin (4.2 ml) and sodium borohydride (2.03 g) are added to the solution under ice-cooling. The mixture is adjusted to pH 6 with hydrogen chloride/methanol solution and is stirred at room temperature for 2 hours. The mixture is acidified with diluted hydrochloric acid and stirred for 15 minutes to decompose excess sodium borohydride. The mixture is alkalized with an aqueous potassium carbonate solution and extracted with ethyl acetate. The extract is washed with an aqueous saturated sodium chloride solution, dried and concentrated to remove solvent. The residue is purified by silica gel column chromatography (solvent, n-hexane:ethyl acetate=3:1), whereby 1-ethyl-3-(3,4,5-trimethoxyphenylthio)-1-(2-thienyl)-N,N-dimethylpropylamine (3.2 g) is obtained as colorless oil. Yield: 76.2%.

IR$\nu_{max}^{film}$(cm$^{-1}$): 1590.
MS(m/e): 395 (M+).
NMR(CDCl$_3$)δ: 0.83(3H, t), 1.86(2H, q), 2.13(6H, s), 2.0– 2.35(2H, m), 2.65–3.15(2H, m), 3.75, 3.77(9H, s, s), 6.62(2H, s), 6.7–7.4(3H, m).
Maleate of the product:
m.p. 118°–119° C. (recrystallized from ethanol).

EXAMPLE 31

(1) 1-Ethyl-3-(4-methylphenylthio)-1-(2-thienyl)propyl isocyanide (4.02 g) is treated in the same manner as described in Example 30-(1), whereby 1-ethyl-3-(4-methylphenylthio)-1-(2thienyl)propylamine (3.74 g) is obtained as colorless oil.
Yield: 96.2%.
MS(m/e): 291 (M+).
NMR(CDCl$_3$)δ: 0.80(3H, t), 1.57(2H, s), 1.65–2.20(4H, m), 2.29(3H, s), 2.46–3.15(2H, m), 6.75–7.30(7H, m).

(2) The product (3.7 g) obtained in Paragraph (1) is treated in the same manner as described in Example 30-(2), whereby 1-ethyl-3-(4-methylphenylthio)-1-(2-thienyl)-N,N-dimethylpropylamine (3.4 g) is obtained as colorless oil.
Yield: 84.2%.
MS(m/e): 290 (M+).
NMR(CDCl$_3$)δ: 0.81(3H, t), 1.68–2.50(4H, m), 2.12(6H, s), 2.30(3H, s), 2.58–3.10(2H, m), 6.73–7.40(7H, m).
Hydrochloride of the product:
m.p. 157°–158° C. (recrystallized from ethanol-ether).

EXAMPLE 32

(1) 3-(4-Chlorophenylthio)-1-ethyl-1-(2-thienyl)propyl isocyanide (7.15 g) is treated in the same manner as described in Example 30-(1), whereby 3-(4-chlorophenylthio)-1-ethyl-1-(2thienyl)propylamine (6.61 g) is obtained as an oil. Yield: 95.4%.
MS(m/e): 311 (M+).
NMR(CDCl$_3$)δ: 0.80(3H, t), 1.55(2H, s), 1.60–2.20 (4H, m), 2.54–3.10(2H, m), 6.70–7.34(7H, m).

(2) The product (6.61 g) obtained in Paragraph (1) is treated in the same manner as described in Example 30-(2), whereby 1-ethyl-3-(4-chlorophenylthio)-1-(2-thienyl)-N,N-dimethylpropylamine (6.47 g) is obtained as colorless oil.
Yield: 89.8%.
IR$\nu_{max}^{film}$(cm-1): 1475.
MS(m/e): 310 (M+—C$_2$H$_5$).
NMR(CDCl$_3$)δ: 0.83(3H, t), 2.13(6H, s), 1.65–2.47(4H, m), 2.60–3.20(2H, m), 6.74–6.85(1H, m), 6.90–7.08(1H, m), 7.13–7.42(5H, m).
Hydrochloride of the product:
Colorless crystals. m.p. 174°–175° C. (recrystallized from ethanol-ether).

EXAMPLE 33

1-Ethyl-3-(3,4,5-trimethoxyphenyloxy)-1-(2-thienyl)-propyl isocyanide (3.3 g) is treated in the same manner as described in Example 30-(1) and (2), whereby 1-ethyl-3-(3,4,5-trimethoxyphenyloxy)-1-(2-thienyl)-N,N-dimethylpropylamine (2.45 g) is obtained.
Yield: 71%.
NMR(CDCl$_3$)δ: 0.96(3H, t), 1.80–2.65(4H, m), 2.20(6H, s), 3.76(3H, s), 3.82(6H, s), 3.75–4.25(2H, m), 6.12 (2H, s), 6.84–7.10(2H, m), 7.15–7.30(1H, m).
Maleate of the product:
m.p. 125°–126° C. (recrystallized from ethanol).

EXAMPLE 34

Sodium hydride (63.5% oil dispersion, 0.66 g) is added to a solution of thiocresol (2.2 g) in toluene (40 ml) under ice-cooling and the mixture is stirred at room temperature for 30 minutes. A solution of 1-(3,4,5-trimethoxybenzyloxymethyl)-1-(2-thienyl)-N,N-dimethylpropylamine (2.2 g) in toluene (20 ml) is added to the mixture under ice-cooling and hexamethylphosphoric triamide (3 ml) is added thereto. The mixture is refluxed in nitrogen atmosphere for 5 hours. After cooling, 10% hydrochloric acid is added to the mixture and the aqueous layer is collected therefrom. The aqueous layer is washed with ether and adjusted to pH 8 with sodium bicarbonate and then extracted with ether. The extract is dried and concentrated under reduced pressure to remove solvent. The residue is purified by silica gel column chromatography (solvent, chloroform:ethanol=100:1). The resulting product is recrystallized from a mixture of ethyl acetate and n-hexane, whereby 1-(4-hydroxy-3,5-dimethoxybenzyloxymethyl)-1-(2-thienyl)-N,N-dimethylpropylamine (2 g) is obtained as colorless pillars.
Yield: 94%.
m.p. 126°–127° C.
IR$\nu_{max}^{Nujol}$(cm$^{-1}$): 3300, 2900, 1620.
MS(m/e): 365 (M+).
NMR(CDCl$_3$)δ: 0.78(3H, t), 1.82–2.12(2H, m), 2.22, (6H, s), 3.62, 3,76(2H, AB$_q$, J=9 Hz), 3.80(6H, s), 4.40 (2H, s), 6.45(2H, s), 6.6–7.1(3H,m).

EXAMPLE 35

2-Dimethylamino-2-(2-thienyl)butyl 3,4,5-trimethoxybenzoate (2.1 g) is treated in the same manner as described in Example 34, whereby 2-dimethylamino-2-(2-thienyl)butyl 4-hydroxy-3,5-dimethoxybenzoate (1.8 g) is obtained as colorless crystals.
Yield: 89%.
IR$\nu_{max}^{Nujol}$(cm$^{-1}$): 3300, 1690, 1600.
MS(m/e): (M+—C$_2$H$_5$).
NMR(CDCl$_3$)δ: 0.87(3H, t), 2.04(2H, q), 2.40(6H, s), 3.90 (6H, s), 4.73(2H, s), 6.9–7.3(3H, m), 7.3(2H, s).

EXAMPLE 36

1-Ethyl-3-(3,4,5-trimethoxyphenylthio)-1-(2-thienyl)-N,N-dimethylpropylamine (1.42 g) is treated in the same manner as described in Example 34, whereby 1-ethyl-3-(4-hydroxy-3,5-dimethoxyphenylthio)-1-(2-thienyl)-N,N-dimethylpropylamine (0.86 g) is obtained as colorless prisms. Yield: 62.3%.
m.p. 78°–80° C.
IR$\nu_{max}^{Nujol}$(cm$^{-1}$):3200, 1600.
MS(m/e): 381 (M+).
NMR(CDCl$_3$)δ:. 0.82(3H, s), 1.76–2.30(4H, m), 2.10 (6H, s), 2.65–3.0(2H, m), 3.86(6H, s), 6.67(2H,s), 6.7–7.3 (3H, m).

EXAMPLE 37

1-(3,4,5-Trimethoxybenzyloxymethyl)-1-(3-thienyl)-N,N-dimethylpropylamine (2 g) is treated in the same manner as described in Example 34, whereby 1-(4-hydroxy-3,5-dimethoxy-benzyloxymethyl)-1-(3-thienyl)-N,N-dimethylpropylamine (0.7 g) is obtained.
m.p. 147°–148° C. (recrystallized from ethyl acetate).
IR$\nu_{max}^{Nujol}$(cm$^{-1}$): 3200, 1610.
NMR(CDCl$_3$)δ: 0.73 (3H, t), 1.96(2H, q), 2.21(6H, s), 3.76, 3.83(2H, AB$_q$), 3.85(2H, s), 4.48(2H, s), 6.57 (2H, s), 7.–7.3(3H, m).

EXAMPLE 38

Sodium methoxide (0.4 g) is added to a solution of 2-dimethylamino-2-(2-thienyl)-1-butanol (7.5 g) and methyl 4-amino-3-chloro-2-methoxybenzoate (16.2 g) in toluene (150 ml) and the mixture is stirred at 110° C. for 96 hours while removing methanol which is produced during the reaction. After cooling, the mixture is washed with water, dried and concentrated to remove solvent. The residue is purified by silica gel column chromatography (solvent, chloroform:ethanol=50:1), whereby 2-dimethylamino-2-(2-thienyl)butyl 4-amino-3-chloro-2-methoxybenzoate (3.6 g) is obtained as colorless crystals.

m.p. 110°–112° C. (recrystallized from ethyl acetate-n-hexane).

IR$\nu_{max}^{Nujol}$(cm$^{-1}$): 3500, 3400, 1690, 1620.

NMR(CDCl$_3$)δ: 0.85(3H, t), 2.10(2H, m), 2.35(6H, s), 3.78(3H, s), 4.48(2H, broad s), 4.66(2H, s), 6.27 (1H, s), 6.9–7.3(3H, m), 7.77(1H, s).

EXAMPLE 39

(1-a) 2-Dimethylamino-2-(2-thienyl)-1-butanol (11.2 g) and L-(+)-tartaric acid (4.2 g) are dissolved in methanol with heating and the solution is concentrated to remove solvent. Ethanol is added to the residue and the mixture is allowed to stand overnight. The precipitates are collected by filtration and recrystallized from ethanol, whereby (+)-2- dimethylamino-2-(2-thienyl)-1-butanol·L-(+)-tartarate (6.5 g) is obtained. An aqueous potassium carbonate solution is added to the salt and the mixture is extracted with chloroform. The extract is dried and concentrated to remove solvent. The residue is crystallized with n-hexane, whereby (+)-2-dimethylamino-2-(2-thienyl)-1-butanol (2.7 g) is obtained.

m.p. 90°–91° C.

$[\alpha]_D^{18}$ +26.2° (c=1, chloroform).

(1-b) The mother liquor which is obtained during the resolution operation in Paragraph (1-a) is concentrated to remove solvent. An aqueous 10% potassium carbonate solution is added to the residue and the mixture is extracted with ethyl acetate. The extract is washed with an aqueous saturated sodium chloride solution, dried and concentrated under reduced pressure to remove solvent. The residue and D-(−)-tartaric acid (4.2 g) are dissolved in ethanol (50 ml) with heating and the solution is allowed to stand overnight. The precipitates are collected by filtration and recrystallized from ethanol, whereby (−)-2-dimethylamino-2-(2-thienyl)-1- butanol'D-(-)-tartarate (4.2 g) is obtained. The salt is treated in the same manner as described in the above-mentioned (1-a), whereby (−)-2-dimethylamino-2-(2-thienyl)-1-butanol (1.5 g) is obtained.

m.p. 90°–91° C.

$[\alpha]_D^{18}$ −26.3° (c=1, chloroform).

(2) The product obtained in Paragraph (1-a) or (1-b) and benzoyl chloride (0.85 g) are treated in the same manner as described in Example 1-(2), whereby the following compounds are obtained.

(a) (−)-2-Dimethylamino-2-(2-thienyl)butyl benzoate
Colorless oil, Yield: 1.1 g (72.3%).
Maleate:
m.p. 80°–83° C. (recrystallized from ethyl acetate).
$[\alpha]_D^{18}$ −9.6° (c=1, pyridine).

(b) (+)-2-Dimethylamino-2-(2-thienyl)butyl benzoate
Colorless oil, Yield: 1.2 g (78.9%).
Maleate:
m.p. 82°–84° C. (recrystallized from ethyl acetate).
$[\alpha]_D^{18}$ +9.9° (c=1, pyridine).

EXAMPLE 40

(1-a) 2-Dimethylamino-2-(2-thienyl)butyl 3,4,5-trimethoxybenzoate (33.1 g) and L-(+)-tartaric acid (6.3 g) are dissolved in ethanol (200 ml) with heating and the solution is allowed to stand at room temperature overnight. The precipitates are collected by filtration, washed with ethanol and ether, dried and recrystallized from ethanol, whereby (+)-2-dimethylamino-2-(2-thienyl)butyl 3,4,5-trimethoxybenzoate·L-(+)-tartarate (14 g) is obtained.

m.p. 149°–151° C.

$[\alpha]_D^{18}$ +10.7° (c=1, methanol).

(1-b). The mother liquor which is obtained during the resolution operation in Paragraph (1) is concentrated to remove solvent. An aqueous potassium carbonate solution is added to the residue and the mixture is extracted with ethyl acetate. The extract is washed with a saturated sodium chloride solution, dried and concentrated to remove solvent. The residue and D-(−)-tartaric acid (6.3 g) are dissolved in ethanol (200 ml) with heating and the solution is allowed to stand overnight. The precipitates are collected by filtration and recrystallized from ethanol, whereby (−)-2-dimethylamino-2(2-thienyl)butyl 3,4,5-trimethoxybenzoate·D-(−)-tartarate (16 g) is obtained.

m.p. 149°–151° C. $[\alpha]_D^{18}$ −10.7° (c=1, methanol).

(2) The salt obtained in Paragraph (1-a) or (1-b) is treated with an alkali agent and the resulting compound (free base) is converted to maleate thereof, whereby the following compounds are obtained.

(a) (+)-2-Dimethylamino-2-(2-thienyl)butyl 3,4,5-trimethoxybenzoate maleate
m.p. 91°–93° C. (recrystallized from ethyl acetate isopropyl ether).
$[\alpha]_D^{18}$ +5.7° (c=1, pyridine).

(b) (−)-2-Dimethylamino-2-(2-thienyl)butyl 3,4,5-trimethoxybenzoate maleate.
m.p. 91°–93° C. (recrystallized from ethyl acetate-isopropyl ether).
$[\alpha \cdot _D^{18}$ 5.8° (c=1, pyridine).

PREPARATION OF STARTING COMPOUNDS

Preparation 1

(1) A mixture of 2-propionylthiophene (50 g), sodium cyanide (19.9 g), ammonium bicarbonate (106 g) and an aqueous methanol solution is stirred for 5 hours under increased pressure with heating. After cooling, the precipitates are collected by filtration, washed and dried, whereby 5-ethyl-5-(2-thienyl)hydantoin (45 g) is obtained.

m.p. 173°–174° C.

(2) A mixture of the product (12.3 g) obtained in Paragraph (1) and 20% aqueous sodium hydroxide solution (68 g) is stirred for 5 hours under increased pressure with heating. After cooling, the mixture is chromatographed on a column packed with a strong acidic ion exchange resin, followed by eluting with an aqueous 5% ammonia solution. The eluates is concentrated under reduced pressure to remove solvent and the crude crystals thus obtained are recrystallized from an aqueous diluted ammonia solution, whereby 2-amino-(2-thienyl)butyric acid (8.96 g) is obtained.

IR$\nu_{max}^{Nujol}$(cm $^{-1}$): 1620, 1600.

(3) A mixture of the product (18.5 g) obtained in Paragraph (2), methanol (74 ml) and concentrated sulfuric acid (13 g) is stirred for 3 days with heating. After cooling, the mixture is concentrated under reduced pressure to remove methanol, and ice-water is added to the residue. The aqueous mixture is alkalized with an aqueous ammonia solution and extracted with ethyl acetate. The extract is washed, dried and concentrated to remove solvent. The residue is distilled under reduced pressure, whereby methyl 2-amino-2-(2-thienyl)butyrate (16.1 g) is obtained.

IR$\nu_{max}^{film}$(cm$^{-1}$): 3400, 3300, 1735.

(4) A mixture of the product (10 g) obtained in Paragraph (3), 35% formalin (12.9 g) and formic acid (11.5 g) is stirred for 15 minutes with heating. After cooling, the mixture is alkalized with potassium carbonate and extracted with ethyl acetate. The ethyl acetate extract is extracted with 5% hydrochloric acid and the extract is further alkalized and then is extracted with ethyl acetate. The extract is washed, dried and concentarated under reduced pressure to remove solvent, whereby methyl 2-dimethylamino-2-(2-thienyl)butyrate (9 g) is obtained.

IR$\nu_{max}^{film}$:1720.

The corresponding starting compounds are treated in the same manner as described above, whereby ethyl 2-dimethylamino-2-(2-thienyl)propionate is obtained.

IR$\nu_{max}^{film}$ (cm$^{-1}$): 1730.

Preparation 2

(1) Methyl 2-amino-2-(2-thienyl)butyrate (11.94 g) is dissolved in hexamethylphosphoric triamide (200 ml), and ethyl iodide (28.7 g) and potassium carbonate (37.3 g) is added thereto. The mixture is stirred at room temperature for 4 hours and further stirred at 70° C. for one hour. Water is added to the reaction mixture and the mixture is extracted with ether. The extract is washed with water, dried and concentrated to remove solvent. The residue is purified by silica gel column chromatography, whereby methyl 2-ethylamino-2-(2-thienyl)butyrate (8.99 g) is obtained.

IR$\nu_{max}^{Nujol}$(cm$^{-1}$): 1735.

(2) The product (6.72 g) obtained in Paragraph (1) is dissolved in acetic acid (52 ml) and sodium borohydride (5.11 g) is added thereto. The mixture is stirred at 55° C. for 16 hours and water is added to the mixture. The aqueous mixture is neutralized with sodium hydroxide and extracted with ethyl acetate. The extract is washed with water, dried and concentrated to remove solvent. The residue is purified by silica gel column chromatography, whereby methyl 2-diethylamino-2-(2-thienyl)butyrate (5.23 g) is obtained.

IR$\nu_{max}^{Nujol}$(cm$^{-1}$): 1725.

Preparation 3

(1) 2-Amino-2-(3-thienyl)acetic acid (10 g) is dissolved in 1N sodium hydroxide solution, and 1N sodium hydroxide solution and a solution of benzyloxycarbonyl chloride (13 g) in ether are simultaneously added dropwise thereto at 5° to 10° C. with vigorous stirring. The mixture is stirred at the same temperature for 3 hours. After the reaction mixture is washed, the mixture is acidified and extracted with ethyl acetate. The extract is washed, dried and concentrated to remove solvent. The residue is crystallized with a mixture of ethyl acetate and diisopropyl ether, whereby 2-benzyloxycarbonylamino-2-(3-thienyl)acetic acid (13.6 g) is obtained. m.p. 115°–117° C.

(2) The product (13.6 g) obtained in Paragraph (1) is added to a solution of thionyl chloride (6.7 g) in ethanol and the mixture is stirred for 3 hours with stirring. After cooling, the mixture is concentrated to remove solvent and the residue is dissolved in water and then extracted with ethyl acetate. The extract is washed, dried and concentrated to remove solvent, whereby ethyl 2-benzyloxycarbonylamino-2-(3-thienyl)acetate (14.5 g) is obtained.

IR$\nu_{max}^{film}$(cm$^{-1}$): 3300, 1740, 1720.

(3) The product (14.9 g) obtained in Paragraph (2) is dissolved in dimethylformamide, and sodium hydride (60% oil dispersion, 1.87 g) is added thereto at a temperature below 10° C. The mixture is stirred at 5° to 10° C. for one hour and ethyl iodide (10.9 g) is added thereto. The mixture is stirred at room temperature for 16 hours and concentrated under reduced pressure to remove solvent. The residue is dissolved in a mixture of ethyl acetate and an aqueous saturated sodium chloride solution. The organic layer is collected, dried and concentrated to remove solvent. The residue is purified by silica gel chromatography, whereby ethyl 2-benzyloxycarbonylamino-2-(3-thienyl)butyrate (11.1 g) is obtained.

IR$\nu_{max}^{film}$(cm$^{-1}$): 3300, 1720.

(4) Hydrogen bromide/acetic acid solution (25 ml) is added to the product (11.1 g) obtained in Paragraph (3) and the mixture is stirred at room temperature for one hour. The mixture is concentrated under reduced pressure to remove solvent. Benzene is added to the residue and the mixture is concentrated under reduced pressure to remove solvent. The residue is crystallized with ether, whereby ethyl 2-amino-2-(3-thienyl)butyrate hydrobromide (6.5 g) is obtained.

m.p. 193°–194° C.

(5) The product (10.2 g) obtained in Paragraph (4) is alkalized with an aqueous potassium carbonate solution and extracted with ethyl acetate. The extract is washed, dried and concentrated to remove solvent. 35% Formalin (8.3 ml) and formic acid (7.8 ml) are added to the residue and the mixture is stirred for one hour with heating. After cooling, the mixture is alkalized with an aqueous potassium carbonate solution and extracted with ethyl acetate. The extract is washed, dried and concentrated under reduced pressure to remove solvent. The residue is purified by silica gel column chromatography, whereby ethyl 2-dimethylamino-2-(3thienyl)butyrate (7.1 g) is obtained.

IR$\nu_{max}^{film}$(cm$^{-1}$): 1720.

Preparation 4

A solution of diisopropylamine (2.65 g) in tetrahydrofuran is cooled to −60° C. and 1.6M n-butyl lithium/hexane solution (14 ml) is added dropwise thereto in nitrogen atmosphere. The mixture is stirred at the same temperature, whereby the solution containing lithium diisopropylamide is obtained. A solution of 1-(2-thienyl)propyl isocyanide (2.8 g) in tetrahydrofuran is added dropwise to the solution obtained above at −60° C. and the mixture is stirred at the same temperature for 20 minutes. A solution of 2-(3,4,5-trimethoxyphenylthio)ethyl chloride (5.9 g) in tetrahydrofuran is added dropwise to the mixture at −60° C. and the mixture is stirred at −30° C. in nitrogen atmosphere for 2 hours. Acetic acid is added to the mixture to cease the reaction and ether is added to the reaction mixture. The mixture is washed, dried and concentrated under reduced pressure to remove solvent. The residue is purified by silica gel chromatography, whereby 1-ethyl-3-(3,4,5-trimethoxyphenylthio)-1-(2-thienyl)propyl isocyanide (5.2 g) is obtained as red oil.

The corresponding starting compounds are treated in the same manner as described above, whereby the following compounds are obtained.

(i) 1-Ethyl-3-(4-methylphenylthio)-1-(2-thienyl)propyl isocyanide
IR$\nu_{max}^{film}$(cm$^{-1}$): 2120.

(ii) 3-(4-Chlorophenylthio)-1-ethyl-1-(2-thienyl)propyl isocyanide
IR$\nu_{max}^{film}$(cm$^{-1}$): 2120.

(iii) 1-Ethyl-3-(3,4,5-trimethoxyphenyloxy)-1-(2-thienyl)propyl isocyanide
IR$\nu_{max}^{film}$(cm$^{-1}$): 214.

What we claim is:

1. A thiophen derivative of the formula:

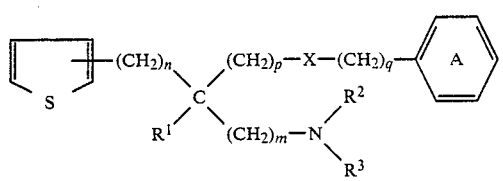

(I)

wherein $R^1$, $R^2$ and $R^3$ are a lower alkyl group, Ring A is phenyl, a lower alkylenedioxy-substituted phenyl, a phenyl group having 1 to 3 substituent(s) selected from the group consisting of a lower alkyl group, a lower alkylthio group, a lower alkoxy group, a phenyl-lower alkoxy group, a lower alkoxycarbonyl group, a halogen atom, amino group and hydroxy group, X is —OCO—, —O— or —S—, m and n are an integer of zero or 1, and p and q are an integer of zero, 1 or 2, or a salt thereof.

2. The compound claimed in claim 1, in which $R^1$, $R^2$ and $R_3$ are methyl or ethyl; Ring A is phenyl, methylenedioxy substituted phenyl, or phenyl having 1 to 3 substituent(s) selected from the group consisting of methyl, n-propyl, tert.-butyl, methylthio, methoxy, benzyloxy, methoxycarbonyl, chlorine, amino and hydroxy.

3. The compound claimed in claim 2, in which Ring A is phenyl, 3,4-methylenedioxyphenyl, 4-methylphenyl, 4-methylthiophenyl 3-methoxyphenyl, 4-methoxyphenyl, 2,4-dimethoxyphenyl, 3,4-dimethoxyphenyl, 2,3,4-trimethoxyphenyl, 3,4,5-trimethoxyphenyl, 2-benzyloxy-3-methoxyphenyl, 2-methoxy-5-methoxycarbonylphenyl, 3-methoxy-2-n-propylphenyl, 3,5-ditert.-butyl-4-hydroxyphenyl, 4-hydroxy-3,5-dimethoxyphenyl, 4-chlorophenyl, 2-chloro-5-methoxyphenyl, 4-chloro-3-methoxyphenyl, 5-chloro-2-methoxyphenyl or 4-amino-3-chloro-2-methoxyphenyl.

4. The compound claimed in claim 2, in which $R^1$ is ethyl, $R^2$ and $R_3$ are methyl, Ring A is phenyl, 3,4,5-trimethoxyphenyl or 4-hydroxy-3,5-dimethoxyphenyl.

5. The compound claimed in claim 2, in which $R^1$ is ethyl, $R^2$ and $R_3$ are methyl, Ring A is 3,4,5-trimethoxyphenyl or 4-hydroxy-3,5-dimethoxyphenyl, n and m are zero, p is 1 or 2, and q is zero or 1.

6. The compound claimed in claim 6 which is 1-(4-hydroxy-3,5-dimethoxybenzyloxymethyl)-1-(2-thienyl)-N,N-dimethylpropylamine or a salt thereof.

7. A pharmaceutical composition which comprises a therapeutically effective amount of the compound according to claim 1 and a pharmaceutically acceptable carrier therefor.

8. A method of regulating the motility of the gastrointestinal tracts in a warm-blooded animal which comprises administering to said warm-blooded animal an effective amount of the compound according to claim 1.

* * * * *